United States Patent [19]

Powers et al.

[11] Patent Number: 5,231,198

[45] Date of Patent: Jul. 27, 1993

[54] ASYMMETRIC SYNTHESIS OF HEXAHYDRODIBENZOFURANS BY STEREOSPECIFIC INVERSION OF ORTHO SUBSTITUTED 2-PHENYLCYCLOHEXANOLS

[75] Inventors: Mattew R. Powers, Barto; Frederick A. Golec, Merion Station, both of Pa.

[73] Assignee: Rhone-Poulenc Rorer Pharmaceuticals Inc., Collegeville, Pa.

[21] Appl. No.: 909,541

[22] Filed: Jul. 6, 1992

[51] Int. Cl.$^5$ ................... C07D 307/91; C12P 1/00
[52] U.S. Cl. .................... 549/461; 435/126
[58] Field of Search ........................... 549/461

[56] References Cited

U.S. PATENT DOCUMENTS

| | | | |
|---|---|---|---|
| 4,857,517 | 8/1989 | Youssefyeh et al. | 514/161 |
| 4,859,683 | 8/1989 | Youssefyeh et al. | 514/299 |
| 4,863,921 | 9/1989 | Youssefyeh et al. | 514/230.5 |
| 4,924,010 | 5/1990 | Youssefyeh et al. | 549/355 |
| 4,959,485 | 9/1990 | Youssefyeh et al. | 549/461 |
| 5,086,179 | 2/1992 | Powers et al. | 546/133 |

OTHER PUBLICATIONS

*Organic Synthesis*, vol. 69, pp. 1–10 (1991).

*Primary Examiner*—Bernard Dentz
*Attorney, Agent, or Firm*—James A. Nicholson; Martin F. Savitzky

[57] ABSTRACT

This invention relates to the stereospecific process for the preparation, separation and purification of hexahydrodibenzofurans which are used in the preparation of the 5HT$_3$ compounds. More specifically, the present invention relates to a process for the preparation of substantially optically pure cishexahydrodibenzofuran compounds including at least two chiral fused ring centers which comprises the acidic catalyzed stereospecific ring closure by the intra-molecular inversion of a gamma, i.e. 2', carbon atom of a 2-[(2'-leaving group)cycloalkyl]phenol.

10 Claims, No Drawings

ASYMMETRIC SYNTHESIS OF HEXAHYDRODIBENZOFURANS BY STEREOSPECIFIC INVERSION OF ORTHO SUBSTITUTED 2-PHENYLCYCLOHEXANOLS

FIELD OF THE INVENTION

This invention relates to stereospecific hexahydrodibenzofuran compounds which exhibit $5HT_3$-antagonist properties including unique CNS, anti-emetic and gastric prokinetic activity and which are void of any significant $D_2$ receptor binding affinity. More specifically, this invention relates to the stereospecific process for the preparation, separation and purification of hexahydrodibenzofurans which are used in the preparation of the $5HT_3$ compounds.

5-Hydroxytryptamine, abbreviated "5-HT", is commonly known as serotonin. Serotonin is found throughout the body including the gastrointestinal tract, platelets, spleen and brain, and appears to be involved in a great number of physiological processes such as neurotransmission at certain neurones in the brain, and is implicated in a number of central nervous system (CNS) disorders. Additionally, serotonin appears to act as a local hormone in the periphery; it is released in the gastrointestinal tract, where it increases small intestinal motility, inhibits stomach and colon motility, and stimulates stomach acid production. Serotonin is most likely involved in normal intestinal peristalsis.

The various physiological activities exerted by serotonin are related to the variety of different receptors found on the surface membrane of cells in different body tissue. The first classification of serotonin receptors included two pharmacologically distinct receptors discovered in the guinea pig ileum. The "D" receptor mediates smooth muscle contraction and the "M" receptor involves the depolarization of cholinergic nerves and release of acetylcholine. Three different groups of serotonin receptors have since been identified and the following assignment of receptors has been proposed: D-receptors are $5-HT_2$-receptors; M-receptors are termed $5-HT_3$-receptors; and all other receptors, which are clearly not $5-HT_2$ or $5-HT_3$, have been referred to as $5-HT_1$-like and work is being continued on this classification.

$5-HT_3$-receptors have been located in non-neurological tissue, brain tissue, and a number of peripheral tissues related to different responses. It has been reported that $5-HT_3$-receptors are located on peripheral neurones where they are related to serotonin's (excitatory) depolarizing action. The following subtypes of $5-HT_3$-receptor activity have been reported: action involving postganglionic sympathetic and parasympathetic neurones, leading to depolarization and release of noradrenaline and acetylcholine, respectively ($5-HT_{3B}$ subtype); action on enteric neurones, where serotonin may modulate the level of acetylcholine ($5-HT_{3C}$ subtype); and action on sensory nerves such as those involved in the stimulation of heart nerve endings to produce a reflex bradycardia ($5-HT_{3A}$ subtype), and also in the perception of pain.

Highly selective $5-HT_3$-antagonists have been shown to be very effective at controlling and preventing emesis (vomiting) induced by chemotherapy and radiotherapy in cancer patients. The anti-emetic effects of $5-HT_3$-antagonists in animals exposed to cancer chemotherapy or radiation are similar to those seen following abdominal vagotomy. The antagonist compounds are believed to act by blocking $5-HT_3$-receptors situated on the cell membranes of the tissue forming the vagal afferent input to the emetic coordinating areas on the brain stem.

Serotonin is also believed to be involved in the disorder known as migraine headache. Serotonin released locally within the blood vessels of the head is believed to interact with elements of the perivascular neural plexus of which the afferent, substance P-containing fibers of the trigeminal system are believed relevant to the condition. By activating specific sites on sensory neuronal terminals, serotonin is believed to generate pain directly and also indirectly by enhancing the nociceptive effects of other inflammatory mediators, for example bradykinin. A further consequence of stimulating the afferent neurones would be the local release of substance P and possibly other sensory mediators, either directly or through an axon reflex mechanism, thus providing a further contribution to the vascular changes and pain of migraine. Serotonin is known to cause pain when applied to the exposed blister base or after an intradermal injection; and it also greatly enhances the pain response to bradykinin. In both cases, the pain message is believed to involve specific $5-HT_3$-receptors on the primary afferent neurones.

$5-HT_3$-antagonists are also reported to exert potential antipsychotic effects, and are believed to be involved in anxiety. Although not understood well, the effect is believed to be related to the indirect blocking of serotonin $5-HT_3$-mediated modulation of dopamine activity.

Many workers are investigating various compounds having $5-HT_3$-antagonist activity.

The development of $5-HT_3$ agents originated from work carried out with metoclopramide (Beecham's Maxolon, A.H. Robins' Reglan), which is marketed for use in the treatment of nausea and vomiting at high doses. Metoclopramide is a dopamine antagonist with weak $5-HT_3$-antagonist activity, which becomes more prominent at higher doses. It is reported that the $5-HT_3$ activity and not the dopamine antagonism is primarily responsible for its anti-emetic properties. Other workers are investigating this compound in connection with the pain and vomiting accompanying migraine.

Merrell Dow's compound MDL-72222 is reported to be effective as an acute therapy for migraine, but toxicity problems have reportedly ended work on this compound. Currently four compounds, A.H. Robins' Zacopride, Beecham's BRL-43694, Glaxo's GR-38032F and Sandoz' ICS-205-930 are in clinical trials for use in chemotherapy-induced nausea and vomiting. GR-38032F is also in clinical trials in anxiety and schizophrenia, and reportedly, Zacopride in anxiety, while ICS-205-930 has been shown to be useful in treating carcinoid syndrome.

Compounds reported as gastroprokinetic agents include Beecham's BRL-24924, which is a serotonin-active agent for use in gut motility disorders such as gastric paresis, audition reflux esophagitis, and is known to have also $5-HT_3$-antagonist activity.

Metoclopramide, Zacopride, Cisapride and BRL-24924 are characterized by a carboxamide moiety situated para to the amino group of 2-chloro-5-methoxy aniline. BRL-43694, ICS-205-930, GR-38032F and GR-65630 are characterized by a carbonyl group in the 3-position of indole or N-methyl indole. MDL-72222 is a bridged azabicyclic 2,4-dichlorobenzoate, while Zacopride, BRL-24924, BRL-43694 and ICS-205-930 have also bridged azabicyclic groups in the form of a carboxamide or carboxylic ester.

Bicyclic oxygen containing carboxamide compounds wherein the carboxamide is ortho to the cyclic oxygen moiety are reported to have antiemetic and antipsychotic properties in EPO Publ. No. 0234872.

Preparation of compounds which are stereoisomers can be carried out by using chiral synthesis, i.e., asymmetric induction methods of synthesis. Speaking generally, syntheses with asymmetric induction have been known in the prior art. A synthesis with asymmetric induction is commonly defined as a process in which a chiral unit in an ensemble of substrate molecules induces, by a reaction with achiral units, resulting molecules in such a manner that the stereoisomeric products are produced in unequal amounts. Such an asymmetric synthesis may be of great economic value for excluding or reducing the amount of unwanted isomers when only one of the diastereomers is of use or interest.

The reactants used in an asymmetric synthesis can be at least one chiral component consisting of a chemical reagent, solvent or catalyst. Alternatively, by selection of specific enantiomers as starting compounds, the preferred stereoisomer in a predominant amount can be induced. However, selection of enantiomerically pure intermediates does not always result in a stereoselective synthesis since chirality of an intermediate could be lost due to racemization under one or more sets of reaction conditions. Consequently, synthetic processes typically involve extra reaction steps to accomplish the stereoselective result as well as involve a tedious recrystallization step.

REPORTED DEVELOPMENTS

Among the reported compounds which have valuable antiemetic and antipsychotic properties is 4-[N-(1-azabicyclo[2.2.2]octan-3-yl)]-2-chloro[5a,6,7,8,9,9a-hexahydro]dibenzofurancarboxamide. This racemic compound has eight possible stereoisomers, and it has been reported that 4-[N-(1-azabicyclo[2.2.2]octan-3(S)-yl)]-2-chloro-[5a(S)-9a(S)-(5a,6,7,8,9,9a-hexahydro)]-dibenzofurancarboxamide and 4-[N-(1-azabicyclo[2.2.-2]octan-3(S)-yl)]-2-chloro-[5a(R)-9a(R)-(5a,6,7,8,9,9a-hexahydro)]dibenzofurancarboxamide are of particular importance. Preparation of such isomers can be carried out using racemic intermediates followed by the difficult task of separating the various isomers of the final product.

A chromatographic separation and crystallization step has been reported for the preparation of enantiomeric 5a,6,7,8,9,9a-hexahydrodibenzofurancarboxamides reported to have 5-HT₃-antagonist and gastroprokinetic activity in U.S. Pat. Nos. 4,859,683, 4,857,517, 4,924,010, 4,863,921 and 4,959,485 all of which are assigned to the same assignee as the present application.

In U.S. Pat. No.: 4,863,921, the synthesis of the 5a,6,7,8,9,9a-hexahydrodibenzofurancarboxamides proceeds via condensation of a substituted 5a,6,7,8,9,9a-hexahydrodibenzofuran-4-carboxylic acid or their acid halides or esters with an amine of the formula $H_2N-R$ which results in the corresponding carboxamide. The process terminates with flash chromatographic separation of the isomers and a recrystallization step in a relatively poor overall yield. This synthesis is made difficult by the presence of an acid sensitive chiral center which racemizes under mild acidic conditions.

In U.S. Pat. No. 5,086,179, also assigned to the same assignee as the present application, involves the process of manipulating acid sensitive compounds under acid conditions, the most preferred compounds being acid sensitive carboxylic chiral compounds.

The present invention is based on a discovery that racemic 2-(2'-benzyloxyphenyl)cyclohexanol may be resolved by hydrolysis of its chloroacetate ester with a lipase enzyme. The resolved material may then be debenzolated to give the chiral diol which is then ring closed with p-toluenesulfonyl chloride to give chiral 5a,6,7,8,9,9a-hexahydrodibenzofuran. The result is a stereoselective synthesis using conditions which do not affect the product's chiral centers. Using the present process, specific stereoisomers of a basic fused ring system can be prepared without recourse to known separation techniques to obtain the desired enantiomers. Thus it is possible to prepare [5a(S)-9a(S)-(5a,6,7,8,9,9a-hexahydro)]dibenzofuran and [5a(R)-9a(R)-(5a,6,7,8,9-,9a-hexahydro)]dibenzofuran and related compounds which can be used to prepare the desired carboxamide.

A procedure disclosed in *Organic Synthesis*, vol. 69 (1991) pages 1–10 describes the "Lipase-catalyzed resolution of alcohols via chloroacetate esters". This paper describes the ready access to both the (+)- and (−) antipodes of trans-2-phenylcyclohexanol with the use of a chiral auxiliary to impart dissymmetry. One chiral auxiliary described is lipase (*P. fluorescens*).

SUMMARY OF THE INVENTION

The present invention relates to a process for the preparation of substantially optically pure cis-hexahydrodibenzofuran compounds including at least two chiral fused ring centers which comprises the acidic catalyzed stereospecific ring closure by the intra-molecular inversion of a gamma, i.e. 2', carbon atom of a 2-[(2'-leaving group)cycloalkyl]phenol.

Preferably the ring closure is conducted on 2-(2'-hydroxycycloalkyl)phenols using an arylsulfonic acid or ester or an acid halide with a tertiary amine. The preferred aryl sulfonic acid or ester is p-toluenesulfonic acid or its esters while the preferred arylsulfonyl halide is p-toluenesulfonyl halide preferably with pyridine.

The preferred process for making the preferred compounds described by formula I:

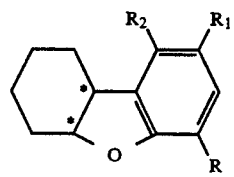

Formula I where
R is hydrogen, COX, COOH or COOR';
X is halo;
R' is alkyl or aralkyl;
R₁ is hydrogen, or halo;
R₂ is hydrogen, nitro, amino or mono- or dialkylamino; and
* denotes a chiral center;
may be carried out on a 2-(2'-leaving group cycloalkyl)-phenol which is a trans compound selected from

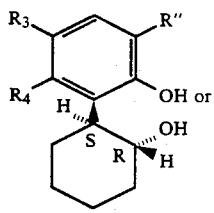

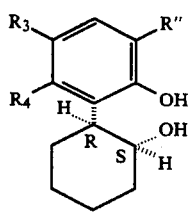

where
R" is hydrogen or COOR';
R' is alkyl or aralkyl; and
R₃ is hydrogen or halo; and
R₄ is hydrogen or nitro.

The preferred compounds prepared by the present process are chiral cis-5a,6,7,8,9,9a-hexahydrodibenzofurans described by Formulae II–III.

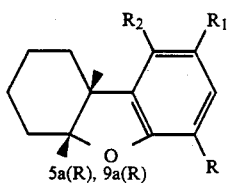

Formula II

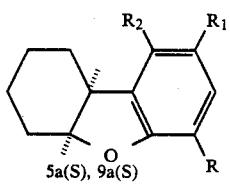

Formula III

Still more preferred are those compounds of Formulae II and III where R is hydrogen or COOH, COOR' where R' is lower alkyl; R₁ is hydrogen or halo; and R₂ is hydrogen, amino or loweralkyl mono- or di-alkyl amino.

The most preferred compounds of this invention are described by Formula III where R is hydrogen or COOH, R₁ is chloro or bromo and R₂ is hydrogen or amino.

Compounds which are prepared by the process of this invention may then be condensed with an amine of the formula H₂N—Z where Z is a cyclic tertiary amine to form an amide having the desired stereochemistry. Amines which may be useful to obtain desired condensation amide products may be found in the above mentioned patents which are assigned to the same assignee as the present application and are hereby incorporated by reference.

DETAILED DESCRIPTION OF THE INVENTION

The following nomenclature is used in the description of this invention.

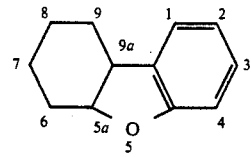

As employed throughout the disclosure, the following terms, unless otherwise indicated, shall be understood to have the following meanings:

"Leaving group" means a group which has the ease of formation from a cycloalkylalcohol and subsequent displacement with a nucleophile. Preferred leaving groups include those formed from arylsulfonic acids, esters or acid halides. The most preferred leaving groups are formed from p-toluenesulfonic acid, p-toluenesulfonates and p-toluenesulfonyl halides.

"Alkyl" means, either alone or within the various substituents, defined hereinbefore, a straight chained or branched hydrocarbon having one to about 20 carbon atoms.

"Lower alkyl" means alkyl having one to about six carbon atoms, for example, methyl, ethyl, propyl, isopropyl, butyl, isobutyl, amyl and hexyl. Preferred lower alkyl includes methyl, ethyl and propyl.

"Halo" means Cl, Br, I and F with chloro being preferred.

"Aralkyl" means an alkyl group substituted by an aryl radical. The preferred aralkyl groups are lower alkyl groups substituted by phenyl or substituted phenyl. The most preferred aralkyl group is benzyl.

"Cycloalkyl" means a cyclic aliphatic group comprising 3 to about 7 carbon atoms. Cyclohexyl is the preferred cycloalkyl group.

The present invention comprises, in a preferred embodiment, the asymmetric synthesis of 5a,6,7,8,9,9a-hexahydrodibenzofurans by enzymatic resolution of ortho substituted 2-phenylcyclohexanols followed by chiral ring closure. The following reaction sequence describes this procedure.

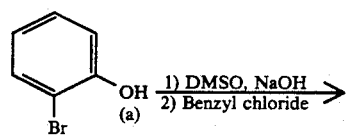

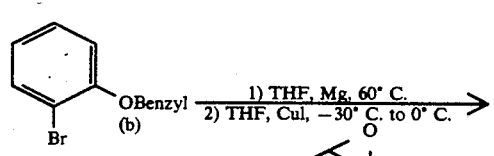

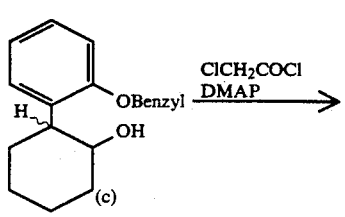

-continued

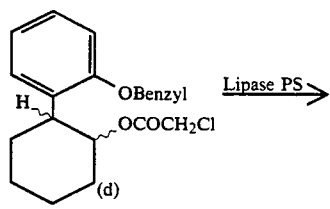

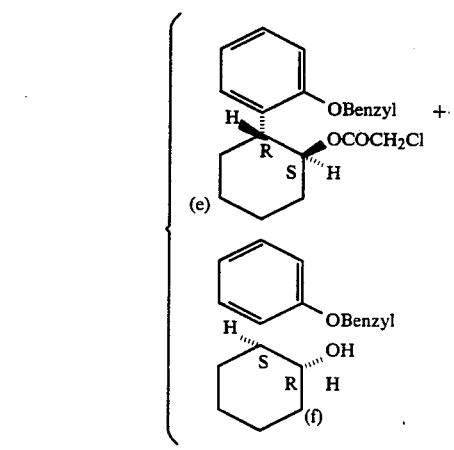

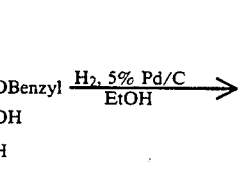

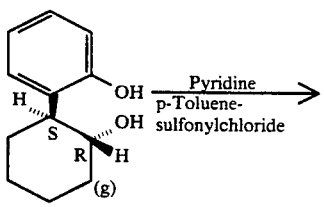

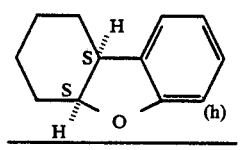

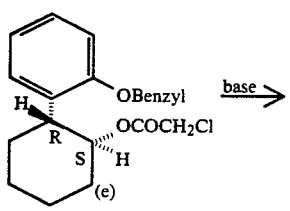

-continued

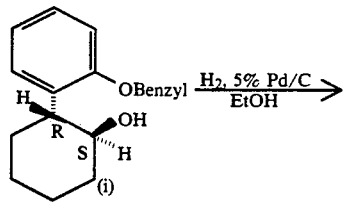

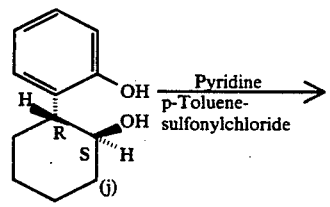

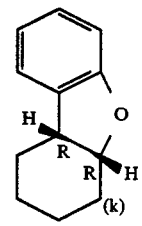

Condensation of benzyl chloride with a halophenol (a) in the presence of a base, results in the benzylated halophenol (b). This is usually carried out in a polar solvent, preferably DMSO at temperatures between −30° to 0° C. The bromo or chlorophenol is preferable and other protecting groups may be used in place of the benzyl group such as other aralkyl groups (such as phenethyl), alkyl, alkoxyalkyl and the like, but the benzyl is preferred.

When a Grignard reaction is carried out on the O-benzylated halobenzene in the normal manner with cyclohexene oxide, the resultant product is the trans-2-(2'-benzyloxyphenyl)cyclohexanol (c). This reaction is carried out in the normal manner in a dry solvent and at lowered temperatures.

Reaction of trans-2-(2'-benzyloxyphenyl)cyclohexanol with chloroacetyl chloride in the presence of 4-dimethylaminopyridine results in racemic trans-2-(2'-benzyloxyphenyl)cyclohexyl chloroacetate (d). This may be carried out at room temperatures or greater depending on the solvent used. The medium should be nonpolar, haloalkanes such as methylene chloride being preferred. Other derivatives of acetic acid may be used in place of chloroacetyl chloride, such as acetyl chloride and trifluoroacetyl chloride.

Treatment of the racemic trans-2-(2'-benzyloxyphenyl)cyclohexyl chloroacetate in a buffered water-/acetone mixture with a lipase PS enzyme results in enantioselective separation of the racemates. To be more specific, formation of trans-(1R,2S)-2-(2'-benzyloxyphenyl)cyclohexanol (f) and trans-(1S,2R)-2-(2'-benzyloxyphenyl)cyclohexyl chloroacetate (e) results. This resolution is carried out in a two phase system, preferably using water and a non polar solvent in a buffered system preferably maintained at pH 7.5-7.8 over an extended period of time from a day to a week and at temperatures between room temperature and 50° C. From the organic layer is recovered the trans-(1R,2S)-2-(2'-benzyloxyphenyl)cyclohexanol (f) and work up of the residues results in the trans-(1S,2R)-2-(2'-benzyloxyphenyl)cyclohexyl chloroacetate (e). This is more fully described in *Organic Synthesis*, Vol. 69 (1991), 1–10.

The removal of the O-protecting group of trans-(1R,2S)-2-(2'-benzyloxyphenyl)cyclohexanol can be carried out in the normal manner by reduction using 5% Pd/C as the catalyst. Chirality is maintained to obtain trans-(1R,2S)-2-(2'-hydroxyphenyl)cyclohexanol (g).

Ring closure of trans-(1R,2S)-2-(2'-hydroxyphenyl)cyclohexanol in the presence of pyridine and p-toluenesulfonyl chloride results in the stereospecific process of inversion to obtain selectively the desired cis-[5a(S)-9a(S)-(5a,6,7,8,9,9a-hexahydro)]dibenzofuran (h). Ring closure may be carried out neet or in a nonpolar solvent, such as toluene and at raised temperatures (50°–80° C.) or at reflux temperatures if a solvent is used, for about 1 to about 4 hrs. The product is extracted out with organic solvent, washed with dil. acid to get rid of any pyridine and p-toluenesulfonyl chloride present. Other tertiary amines may be used such as trialkylamine or amines which would form a quaternary salt with liberated acid.

Ring closure can also be effected by p-toluenesulfonic acid or ester is used this may be done without the presence of pyridine, which is needed to tie-up any HCl liberated.

The present invention results in the stereospecific ring closure in yields of greater than about 50%, most preferably greater than about 65%, and in the most preferred embodiment greater than about 75%.

Cleavage of the chloroacetyl protection group of trans-(1S,2R)-2-(2'-benzyloxyphenyl)cyclohexyl chloroacetate (e) with base, results in trans-(1S,2R)-2-(2'-benzyloxyphenyl)cyclohexanol (i).

Following the above procedures for preparing the [5a(S)-9a(S)-(5a,6,7,8,9,9a-hexahydro)]dibenzofuran (h), when trans-(1S 2R)-2-(2'-benzyloxy-phenyl)cyclohexanol (i) is reduced with 5% Pd/C the trans-(1S,2R)-2-(2'-hydroxyphenyl)cyclohexanol (j) is obtained. This in turn is then ring closed by a stereospecific process of inversion with pyridine in p-toluenesulfonyl chloride to obtain [5a(R),9a(R)-(5a,6,7,8,9,9a-hexahydro)]dibenzofuran If desired, [5a(S),9a(S)-(5a,6,7,8,9,9a-hexahydro)]dibenzofuran and [5a(R),9a(R)-(5a,6,7,8,9,9a-hexahydro)]dibenzofuran may then be treated by known chemical methods to add various substituents onto the hexahydrodibenzofuran ring while maintaining chirality. Thus for example, carbonation of [5a(S),9a(S)-(5a,6,7,8,9,9a-hexahydro)]dibenzofuran with $CO_2$ in the presence of n-butyl-lithium results in [5a(S),9a(S)-(5a,6,7,8,9,9a-hexahydro)]dibenzofuran-4-carboxcylic acid (l). This in turn may be treated with N-chlorosuccinimide in DMF to obtain 2-chloro-[5a(S),9a(S)-(5a,6,7,8,9,9a-hexahydro)]dibenzofuran-4-carboxcylic acid (m). Further, 2-chloro-[5a(S),9a(S)-(5a,6,7,8,9,9a-hexahydro)]dibenzofuran-4-carboxcylic acid may be converted to the acid chloride which may then be treated with (S)-3-aminoquinuclidine to obtain 4-[N-(1-azabicyclo-[2.2.2]octan-3(S)-yl]-2-chloro-[5a(S),9a(S)-(5a,6,7,8,9,9a-hexahydro)]dibenzofuran.

In a similar manner 4-[N-(1-azabicyclo-[2.2.2]octan-3(S)-yl]-2-chloro-[5a(R),9a(R)-(5a,6,7,8,9,9a-hexahydro)]dibenzofuran may be obtained.

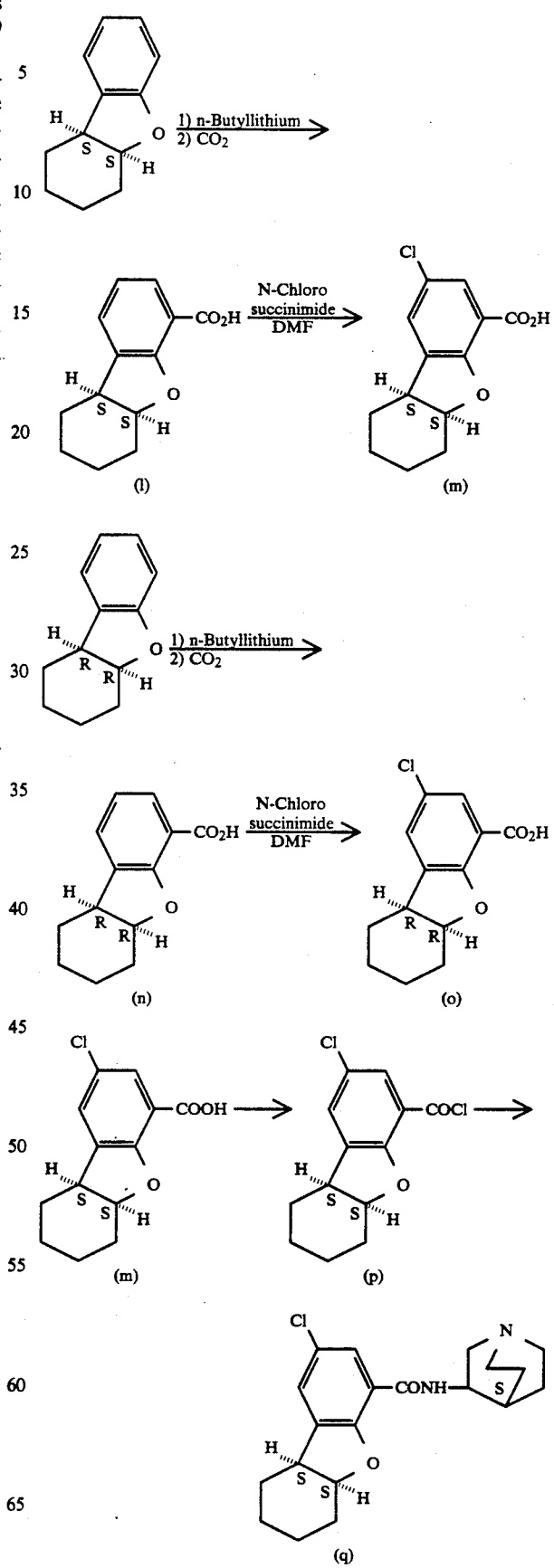

-continued

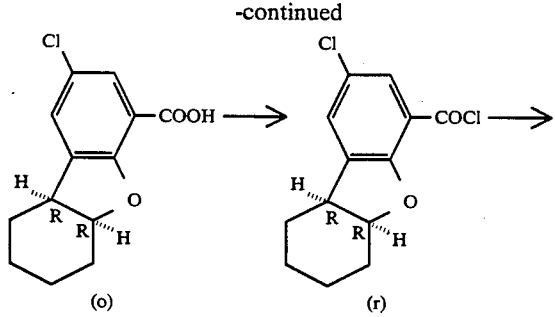

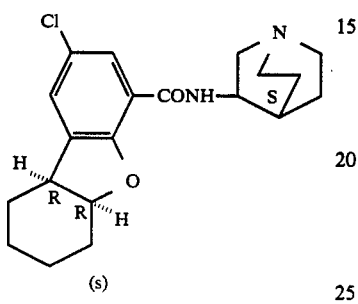

The following examples are given without implying any limitation and are representative to illustrate the present invention.

EXAMPLE 1

2-benzyloxy bromobenzene

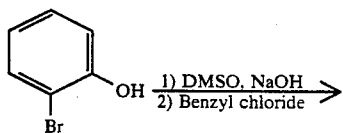

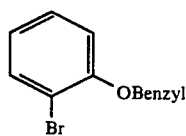

In a 500 ml three neck round bottom flask equipped with a magnetic stirrer, thermometer, condenser, addition funnel and nitrogen inlet, is placed 30 ml of dimethylsulfoxide. Potassium hydroxide (26 g, 0.46 mol.) is added to this followed by the dropwise addition of 2-bromophenol (52 g, 0.3 mol) in 25 ml of dimethylsulfoxide. This solution is stirred for half an hour, then benzylchloride (41 g, 0.324 mol) added dropwise, and the reaction stirred for another 3 hours. The reaction is then poured into 150 ml of ice water and extracted with 100 ml of toluene. The toluene phase is then washed with 50 ml of 1N sodium hydroxide followed by 75 ml of water, dried with magnesium sulfate and evaporated under reduced pressure to yield 50 g of bromophenyl benzylether.

EXAMPLE 2 trans-2-(2'-benzyloxyphenyl)cyclohexanol

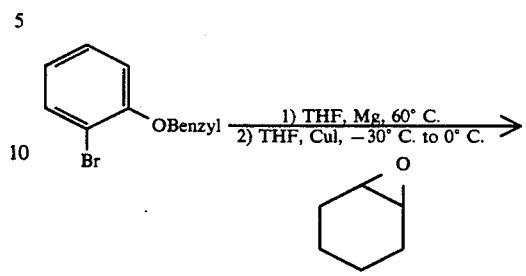

A 1 L round bottom flask equipped with a mechanical stirrer, addition funnel, condenser, and nitrogen inlet is charged with 6.6 g (0.27 mol) of magnesium turnings and 25 ml of dry tetrahydrofuran. To this stirred mixture a solution of 50 g (0.27 mol) of bromophenyl benzylether in 50 ml of dry THF is added dropwise. The reaction needs to be heated (30°-40° C.) at first to initiate it but then the heating mantel is removed and the temperature maintained by the rate of addition. Once the addition is complete the reaction is held at 45°-50° C. for 2 hours, then 300 ml of dry THF is added. The solution is cooled to −30° C. and 1.2 g (0.012 mol) of copper (I) chloride is added. The resulting mixture is stirred for 10 minutes and then a solution of 26 g (0.265 mol) of cyclohexene oxide in 30 ml of THF is added dropwise over 1 hour. Upon completion of the addition the reaction is allowed to warm to 0° C. and stirred for 2 hours, then diluted with 300 ml of ethyl acetate and quenched by addition of 150 ml of saturated aqueous ammonium sulfate solution. The organic phase is separated and washed with another 75 ml of ammonium sulfate solution. The combined aqueous phases are extracted with 100 ml of ethyl acetate. The organic phases are combined, dried with magnesium sulfate, and evaporated under reduced pressure to yield 65 g of trans-2-(2'-benzyloxyphenyl)cyclohexanol as an amber oil, which is used directly in the next step.

EXAMPLE 3 trans-2-(2'-benzyloxyphenyl)cyclohexyl chloroacetate

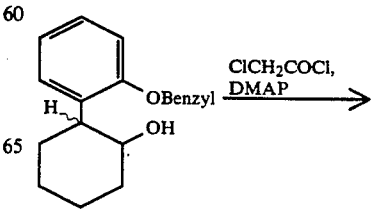

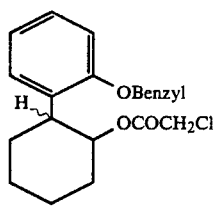

In a 1 L round bottom flask equipped with a magnetic stirrer, thermometer and condenser is placed 65 g (0.23 mol) of trans-2-(2'-benzyloxyphenyl)cyclohexanol. This is dissolved in 200 ml of methylenechloride, and then 28.5 g (0.25 mol) of chloroacetyl chloride is added followed by 0.14 g (0.001 mol) of 4-dimethylaminopyridine. The mixture is heated to reflux and monitored by TLC (silica gel: 20% ethyl acetate, hexane). After 4 hours TLC shows the reaction to be complete, it is cooled to room temperature and 200 ml of saturated sodium bicarbonate is added. The reaction mixture is stirred rapidly for another 3 hours. The organic phase is then separated, dried with anhydrous potassium carbonate, filtered and evaporated under reduced pressure to yield 90 g of an amber oil. This oil is dissolved in 100 ml of hexane from which it crystallizes to afford 74 g of off-white solid trans-2-(2'-benzyloxyphenyl)cyclohexyl chloroacetate, which is used directly in the next step.

EXAMPLE 4

1R,2S-trans-2-(2'-benzyloxyphenyl)cyclohexanol

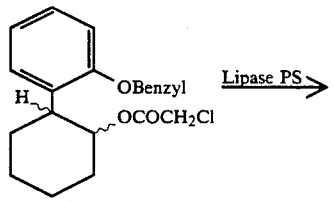

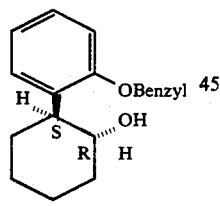

A 250 ml round bottom flask is equipped with a mechanical stirrer, a pH electrode connected to a pH controller, a condenser, a thermometer, and an inlet for sodium hydroxide solution connected to a peristaltic pump. The pump is connected to a 200 ml reservoir of 1N sodium hydroxide. To this system is added 74 g (0.198 mol) of trans-2-(2'-benzyloxyphenyl)cyclohexyl chloroacetate, 75 ml of water, and 5 ml of acetone. This mixture is heated to 50° C. and stirred rapidly. A pH 7 buffer (7 ml) is added to the heterogeneous mixture and then the pH adjusted to 7.5 with 1N sodium hydroxide. Once a steady pH reading is achieved 0.75 g of lipase PS enzyme is added. The pH drops immediately following the addition and base starts to be pumped into the system. The pH of the reaction is held between 7.5 and 7.8. After 2 hours another 1 g of lipase PS is added. The reaction is allowed to run for 4 days until the base addition essentially stops. At this point it is cooled to room temperature and extracted with ethyl acetate (3×150 ml). The combined organic phase is filtered through celite, dried with sodium sulfate, filtered again, and evaporated under reduced pressure. The 55 g of light amber oil obtained is placed on a 250 g silica gel plug, equilibrated with hexane, in a 500 ml sintered glass funnel. This material is then washed through the silica gel with 1.5 L of hexane followed by 3 L of 9:1 hexane:ethyl acetate. Fractions are collected at 250 ml intervals. Fractions 1-7 contain the 2-(2'-benzyloxyphenyl)cyclohexyl chloroacetate which affords 30 g of sticky yellow solids upon standing after removal of the solvent. Fractions 8-18 yields 22 g of the 1R,2S-trans-2-(2'-benzyloxyphenyl)cyclohexanol as a light yellow oil after removal of the solvent: $[\alpha]_D^{r.t.} = -50°$ methanol c=1 mg)

When fractions 1-7 are subjected to basic conditions (2N sodium hydroxide in methanol at reflux for 3 hrs,) to remove the chloroacetate protecting group, then the product prepared is 1S,2R-trans-2-(2'-benzyloxyphenyl)cyclohexanol.

EXAMPLE 5

1R,2S-trans-2-(2'-hydroxyphenyl)cyclohexanol

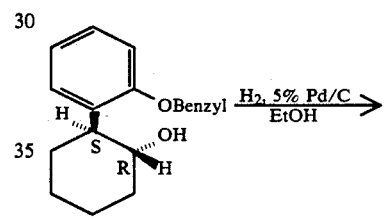

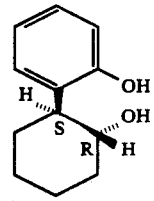

In a 100 ml round bottom flask equipped with a magnetic stirrer, a gas inlet, a septum, a thermometer, and a balloon is placed a solution of 22 g (0.078 mol) of 1R,2S-trans-2-(2'-benzyloxyphenyl)cyclohexanol in 50 ml of ethanol. To this solution is added 0.2 g of 5% palladium on carbon. The reaction is then flushed with nitrogen three times and then filled with hydrogen. The reaction is left to stir under a hydrogen atmosphere for 18 hours. At this point TLC (silica gel: 20% ethyl acetate, hexane) shows no more starting material so the reaction is flushed with nitrogen filtered through celite and evaporated under reduced pressure to yield 13 g of 1R,2S-trans-2-(2'-hydroxyphenyl)cyclohexanol as a clear oil: ($[\alpha]_D^{r.t.} = -27°$ methanol c=1 mg)

When 1R,2S-trans-2-(2'-benzyloxyphenyl)cyclohexanol is replaced by 1S,2R-trans-2-(2'-benzyloxyphenyl)-cyclohexanol, then the product prepared is 1S,2R-trans-2-(2'-hydroxyphenyl)cyclohexanol.

EXAMPLE 6

[5a(S),9a(S)-(5a,6,7,8,9,9a-hexahydro)]dibenzofuran

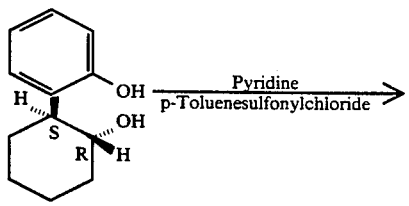

To 1R,2S-trans-2-(2'-hydroxyphenyl)cyclohexanol (1 g) dissolved in 15 ml of dry pyridine under $N_2$ is quickly added 0.8 g of p-toluenesulfonyl chloride. The reaction is heated to 60° C. for 2 hours. The reaction is followed by TLC (hexane:EtOAc; 95:1). The reaction is then stopped, 25 ml of EtOAc is added and this mixture washed with 1N HCl (3×30 ml). The EtOAc solution is then dried and rotoevaporated to give an amber oil (1 g). Filtering this through a silica gel plug with hexane yields 0.7 g of amber oil which NMR shows to be [5a(S),9a(S)-(5a,6,7,8,9,9a-hexahydro)]dibenzofuran (yield=%80) ($[\alpha]_D^{r.t.} = -17°$ methanol c=1 mg).

When 1R,2S-trans-2-(2'-hydroxyphenyl)cyclohexanol is replaced with 1S,2R-trans-2-(2'-hydroxyphenyl)cyclohexanol, then the product prepared is [5a(R),9a(R)-(5a,6,7,8,9,9a-hexahydro)]dibenzofuran.

EXAMPLE 7

[5a(S),9a(S)-(5a,6,7,8,9,9a-hexahydro)]dibenzofuran-4-carboxcylic acid

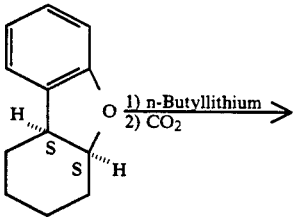

To 40 ml of hexane in a dry 100 ml round bottom flask under $N_2$ is added 1.4 ml of 2.5M n-BuLi in hexane by syringe. To this solution is added 0.4 g of N,N,N'N'-tetramethylethylenediamine dropwise by syringe. The temperature of the reaction mixture is 25° C. This is allowed to stir for 30 min. To the reaction mixture is added with cooling, [5a(S),9a(S)-(5a,6,7,8,9,9a-hexahydro)]dibenzofuran (0.5 g) over a period of 15 min. The reaction mixture is stirred for three hours at 25° C., cooled in an ice bath and $CO_2$ bubbled into the mixture. The reaction mixture turns a cloudy light yellow within a few seconds from an amber color. The reaction is stopped after an hour and a half and placed in the refrigerator overnight. Another 20 ml of hexane is added and the reaction mixture extracted with 1N NaOH (2×60 ml). The combined washes are then acidified with HCl in an ice bath and extracted with toluene (2×60 ml). The toluene extracts are combined, dried with magnesium sulfate and rotovaped to yield 400 mg of [5a(S),9a(S)-(5a,6,7,8,9,9a-hexahydro)]dibenzofuran-4-carboxylic acid as an oil which solidifies upon standing.

When [5a(S),9a(S)-(5a,6,7,8,9,9a-hexahydro)]dibenzofuran is replaced by [5a(R),9a(R)-(5a,6,7,8,9,9a-hexahydro)]dibenzofuran, then the product prepared is [5a(R),9a(R)-(5a,6,7,8,9,9a-hexahydro)]dibenzofuran-4-carboxcylic acid.

EXAMPLE 8

[5a(S),9a(S)-(5a,6,7,8,9,9a-hexahydro)]-2-chlorodibenzofuran-4-carboxcylic acid

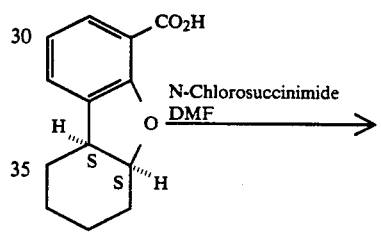

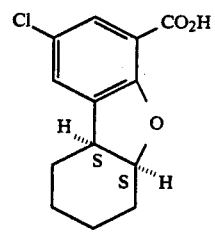

To [5a(S),9a(S)-(5a,6,7,8,9,9a-hexahydro)]dibenzofuran-4-carboxcylic acid (0.4 g) dissolved in 40 ml of DMF is added 0.25 g of N-chloro-succinamide. The reaction is stirred at room temperature for 20 hours. To this reaction reaction mixture is added 40 ml of ethylacetate followed by washing with 1N HCl (50 ml). The organic phase is then washed with water (3×40 ml), dried with magnesium sulfate and evaporated under reduced pressure to yield 400 mg of 2-chloro-[5a(S),9a(S)-(5a,6,7,8,9,9a-hexahydro)]dibenzofuran-4-carboxcylic acid as a white solid.

When [5a(S),9a(S)-(5a,6,7,8,9,9a-hexahydro)]dibenzofuran-4-carboxcylic acid is replaced with [5a(R),9a(R)-(5a,6,7,8,9,9a-hexahydro)]dibenzofuran-4-carboxcylic acid is replaced with [5a(R),9a(R)-(5a,6,7,8,9,9a-hexahydro)]dibenzofuran-4-carboxcylic acid, then the product prepared is 2-chloro-[5a(R),9a(R)-(5a,6,7,8,9,9a-hexahydro)]dibenzofuran-4-carboxcylic acid.

EXAMPLE 9

5-chloro-2-benzyloxybromobenzene

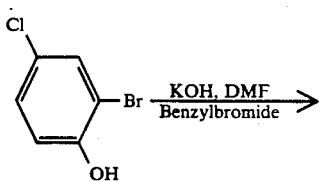

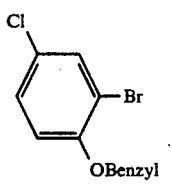

In a 500 ml three neck round bottom flask equipped with a magnetic stirrer, thermometer, condenser, addition funnel and nitrogen inlet, is placed 30 ml of dimethylsulfoxide. Potassium hydroxide (20 g, 0.36 mol.) is added to this followed by the dropwise addition of 2-bromo-4-chlorophenol (50 g, 0.24 mol) in 25 ml of dimethylsulfoxide. This solution is stirred for half an hour, then benzylbromide (41 g, 0.24 mol) is added dropwise, and the reaction stirred for another 3 hours. The reaction is then poured into 150 ml of ice water and extracted with 100 ml of toluene. The toluene phase is washed with 50 ml of 1N sodium hydroxide followed by 75 ml of water, dried with magnesium sulfate and evaporated under reduced pressure to yield 65 g of 2-bromo-4-chlorophenyl benzylether.

EXAMPLE 10 trans-2-(2'-benzyloxy-5'-chlorophenyl)cyclohexanol

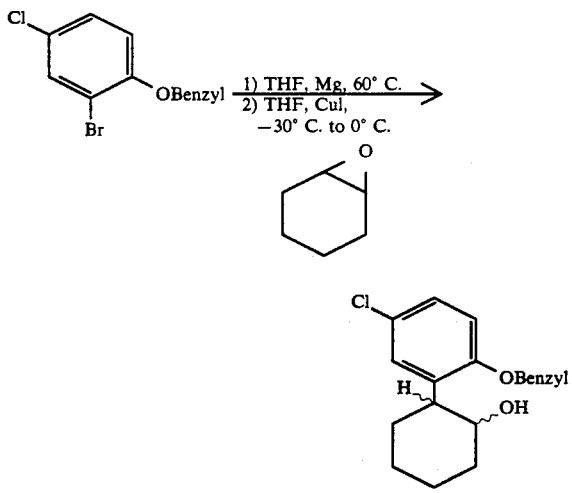

A 1 L round bottom flask equipped with a mechanical stirrer, addition funnel, condenser, and nitrogen inlet is charged with 4.9 g (0.20 mol) of magnesium turnings and 25 ml of dry tetrahydrofuran. To this stirred mixture a solution of 60 g (0.20 mol) of 2-bromo-4-chlorophenyl benzylether in 50 ml of dry THF is added dropwise. The reaction needs to be heated (30°–40° C.) at first to initiate it but then the heating mantel is removed and the temperature maintained by the rate of addition. Once the addition is complete the reaction is held at 60° C. for 2 hours, then 300 ml of dry THF is added. The solution is cooled to −30° C. and 1.2 g (0.012 mol) of copper (I) chloride is added. The resulting mixture is stirred for 10 minutes and then a solution of 20 g (0.20 mol) of cyclohexene oxide in 30 ml of THF is added dropwise over 1 hour. Upon completion of the addition the reaction is allowed to warm to 0° C. and stirred for 2 hours, then diluted with 300 ml of ethyl acetate and quenched by addition of 150 ml of saturated aqueous ammonium sulfate solution. The organic phase is separated and washed with another 75 ml of ammonium sulfate solution. The combined aqueous phases are extracted with 100 ml of ethyl acetate. The organic phases are combined, dried with magnesium sulfate, and evaporated under reduced pressure to yield 50 g of the trans-2-(2'-benzyloxy-5'-chlorophenyl)cyclohexanol as an amber oil, which is used directly in the next step.

EXAMPLE 11 trans-2-(2'-benzyloxy-5'-chlorophenyl)cyclohexyl chloroacetate

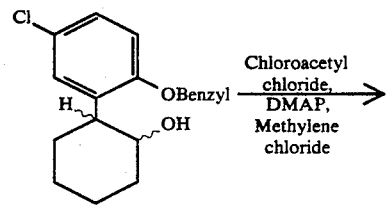

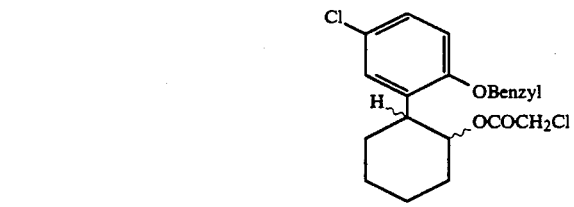

In a 1 L round bottom flask equipped with a magnetic stirrer, thermometer and condenser is placed 50 g (0.15 mol) of trans-2-(2'-benzyloxy-5'-chlorophenyl)cyclohexanol. This is dissolved in 200 ml of methylenechloride, and then 18 g (0.16 mol) of chloracetyl chloride is added followed by 0.14 g (0.001 mol) of 4-dimethylaminopyridine. The mixture is heated to reflux and monitored by TLC (20% ethyl acetate, hexane). After 4 hours TLC shows the reaction to be complete, it is cooled to room temperature and 200 ml of saturated sodium bicarbonate is added. The reaction mixture is stirred rapidly for another 3 hours. The organic phase is then separated, dried with anhydrous potassium carbonate, filtered and evaporated under reduced pressure to yield 70 g of an amber oil. This oil is dissolved in 100 ml of hexane from which it crystallizes to afford 47 g of an off-white solid trans-2-(2'-benzyloxy-5'-chloro-phenyl)-cyclohexyl chloroacetate, which is used directly in the next step.

EXAMPLE 12

1R,2S-trans-2-(2'-benzyloxy-5'-chlorophenyl)cyclohexanol

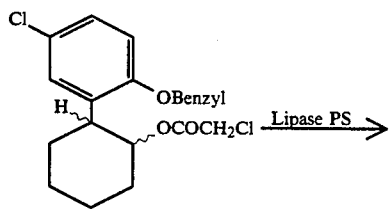

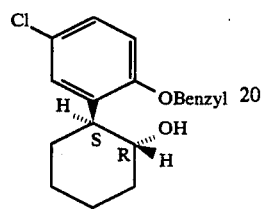

A 250 ml round bottom flask is equipped with a mechanical stirrer, a pH electrode connected to a pH contoller, a condenser, a thermometer, and an inlet for sodium hydroxide solution connected to a peristaltic pump. The pump is connected to a 200 ml reservoir of 1N sodium hydroxide. To this system is added 45 g (0.11 mol) of trans-2-(2'-benzylox-5'-chlorophenyl)cyclohexyl chloroacetate, 50 ml of water, and 3 ml of acetone. This mixture is heated to 50° C. and stirred rapidly. A pH 7 buffer (7 ml) is added to the heterogeneous mixture and then the pH adjusted to 7.5 with 1N sodium hydroxide. Once a steady pH reading is achieved 0.75 g of lipase PS enzyme is added. The pH drops immediately following the addition and base starts to be pumped into the system. The pH of the reaction is held between 7.5 and 7.8. After 2 hours another 1 g of lipase PS is added. The reaction is allowed to run for 8 days. At this point it is cooled to room temperature and extracted with ethyl acetate (3×150 ml). The combined organic phase is filtered through celite, dried with sodium sulfate, filtered again, and evaporated under reduced pressure. The 43 g of light amber oil obtained is placed on a 250 g silica gel plug, equilibrated with hexane, in a 500 ml sintered glass funnel. This material is then washed through the silica gel with 1.5 L of hexane followed by 3 L of 9:1 hexane:ethyl acetate. Fractions are collected at 250 ml intervals. Fractions 1-10 contain the 2-(2'-benzyloxy-5'-chlorophenyl)cyclohexyl chloroacetate which affords 30 g of sticky yellow solids upon standing after removal of the solvent. Fractions 11-18 yield 11 g of the 1R,2S-trans-2-(2'-benzyloxy-5'-chlorophenyl)cyclohexanol as a light yellow oil after removal of the solvent ($[\alpha]_D^{r.t.} = -17°$ methanol c=1 mg).

EXAMPLE 13

1R,2S-trans-2-(2'-hydroxy-5'-chlorophenyl)cyclohexanol

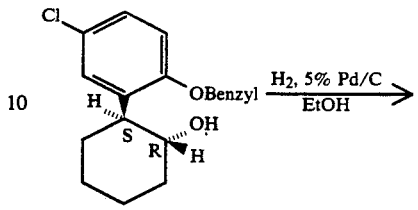

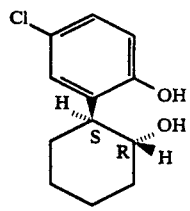

In a 100 ml round bottom flask equipped with a magnetic stirrer, a gas inlet, a septum, a thermometer, and a balloon is placed a solution of 10 g (0.031 mol) of 1R,2S-trans-2-(2'-benzyloxy-5'-chlorophenyl)cyclohexanol in 30 ml of ethanol. To this solution is added 0.1 g of 5% palladium on carbon. The reaction is then flushed with nitrogen three times and then filled with hydrogen. The reaction is left to stir under a hydrogen atmosphere for 18 hours. At this point TLC (20% ethyl acetate, hexane) shows no more starting material so the reaction is flushed with nitrogen, filtered through celite and evaporated under reduced pressure to yield 6 g of 1R,2S-trans-2(2'-hydroxy-5'-chlorophenyl)cyclohexanol as a clear oil ($[\alpha]_D^{r.t.} = -20°$ methanol c=1 mg).

EXAMPLE 14

2-chloro-[5a(S),9a(S)-(5a,6,7,8,9,9a-hexahydro)]dibenzofuran

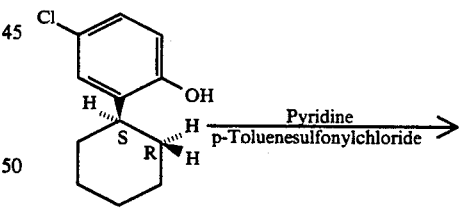

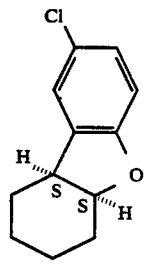

To 1R,2S-trans-2-(2'-hydroxy-5'-chlorophenyl)cyclohexanol (1 g) dissolved in 15 ml of dry pyridine under N₂ is quickly added 0.8 g of p-toluenesulfonyl chloride. The reaction is heated to 60° C. for 2 hours. The reaction is followed by TLC (hexane:EtOAc; 95:1).

The reaction is then stopped, 25 ml of EtOAc is added and this mixture washed with 1N HCl (3×30 ml). The EtOAc solution is then dried and rotoevaporated to give an amber oil (1 g). Filtering this through a silica gel plug with hexane yields 0.7 g of amber oil which NMR shows to be 2-chloro[5a(S),9a(S)-(5a,6,7,8,9,9a-hexahydro)]dibenzofuran ($[\alpha]_D^{r.t.} = -14°$ methanol c=1 mg).

EXAMPLE 15

2-chloro-[5a(S),9a(S)-(5a,6,7,8,9,9a-hexahydro)]dibenzofuran-4-carboxcylic acid

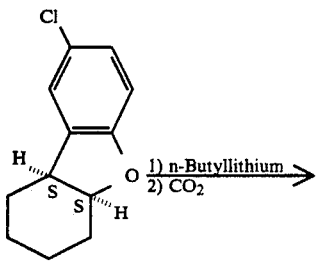

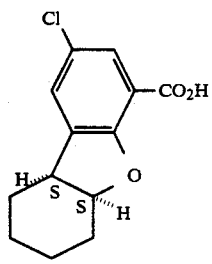

To 40 ml of hexane in a dry 100 ml round bottom flask under $N_2$ is added 1.4 ml of 2.5M n-BuLi in hexane by syringe. To this solution is added 0.4 g of N,N,N'N'-tetramethylethylenediamine dropwise by syringe. The temperature of the reaction mixture is 25° C. This is allowed to stir for 30 min. To the reaction mixture is added with cooling, 2-chloro[5a(S),9a(S)-(5a,6,7,8,9,9a-hexahydro)]dibenzofuran (0.5 g) over a period of 15 min. The reaction mixture is stirred for three hours at 25° C., cooled in an ice bath and $CO_2$ bubbled into the mixture. The reaction mixture turns a cloudy light yellow within a few seconds from an amber color. The reaction is stopped after an hour and a half and placed in the refrigerator overnight. Another 20 ml of hexane is added and the reaction mixture extracted with 1N NaOH (2×60 ml). The combined washes are then acidified with HCl in an ice bath and extracted with toluene (2×60 ml). The toluene extracts are combined, dried with magnesium sulfate and rotovaped to yield 400 mg of 2-chloro[5a(S),9a(S)-(5a,6,7,8,9,9a-hexahydro)]-dibenzofuran-4-carboxcylic acid as an oil which solidifies upon standing. (m. p. 155° C.)

We claim:

1. A process for the preparation of substantially optically pure cishexahydrodibenzofuran compounds including at least two chiral fused ring centers which comprises the acidic catalyzed stereospecific ring closure by the intra-molecular inversion of a gamma carbon atom of a substantially optically pure trans-2-[(2'-leaving group)cycloalkyl]phenol.

2. A process according to claim 1 for the preparation of compounds described by the formula

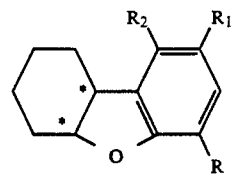

where
R is hydrogen, COX, COOH or COOR';
X is halo;
R' is alkyl or aralkyl;
$R_1$ is hydrogen, or halo;
$R_2$ is hydrogen, nitro, amino or mono- or dialkylamino; and * denotes a chiral center;
wherein said ring closure is conducted with an arylsulfonic acid or ester or an acid halide with a tertiary amine.

3. A process according to claim 2 wherein said ring closure is conducted using p-toluenesulfonic acid or an ester or p-toluenesulfonyl halide with a tertiary amine.

4. A process according to claim 3 where the 2-(2'-leaving group cycloalkyl)phenol is a trans compound selected from

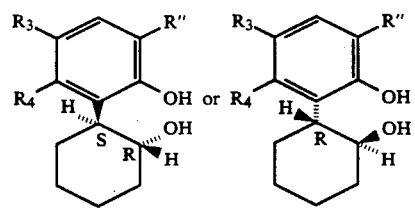

where
R" is hydrogen or COOR';
R' is alkyl or aralkyl; and
$R_3$ is hydrogen or halo; and
$R_4$ is hydrogen or nitro.

5. A process according to claim 4 for the compounds of the formula

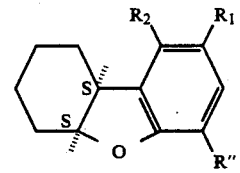

wherein
R" is hydrogen or COOR';
R' is alkyl or aralkyl;
$R_1$ is hydrogen or halo; and
$R_2$ is hydrogen.

6. A process according to claim 4 for the preparation of substantially optically pure compounds of the formula

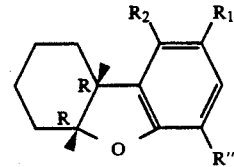

where
- R" is hydrogen or COOR';
- R' is alkyl or aralkyl;
- $R_1$ is hydrogen or halo; and
- $R_2$ is hydrogen.

7. A process according to claim 5 where R", $R_1$ and $R_2$ are all hydrogen.

8. A process according to claim 6 where R", $R_1$ and $R_2$ are all hydrogen.

9. A process according to claim 7 where the reactants are 1R,2S-trans-2-(2'-hydroxyphenyl)cyclohexanol and p-toluenesulfonyl chloride in pyridine.

10. A process for the preparation of substantially optically pure cis-hexahydrodibenzofuran compounds having at least two chiral centers in high yield described by the formula

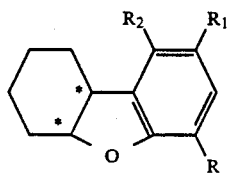

where
- R is hydrogen, COX, COOH or COOR';
- X is halo;
- R' is alkyl or aralkyl;
- $R_1$ is hydrogen, or halo;
- $R_2$ is hydrogen, nitro, amino or mono- or dialkylamino; and * denotes a chiral center;

which comprises:

(a) treating a racemic trans-2-(2'-benzyloxyphenyl)cyclohexyl chloroacetate with a lipase PS enzyme to obtain the corresponding trans-(1R,2S)-2-(2'-benzyloxyphenyl)cyclohexanol and trans-(1S,2R)-2-(2'-benzyloxyphenyl)cyclohexyl chloroacetate;

(b) enantioselectively separating of trans-(1R,2S)-2-(2'-benzyloxyphenyl)cyclohexanol and trans-(1S,2R)-2-(2'-benzyloxyphenyl)cyclohexyl chloroacetate;

(c) cleaving the chloroacetyl protecting group from the trans-(1S,2R)-2-(2'-benzyloxyphenyl)cyclohexyl chloroacetate to obtain trans-(1S,2R)-2-(2'-benzyloxyphenyl)cyclohexanol;

(d) independently removing the O-benzyl protecting group from the trans-(1R,2S)-2-(2'-benzyloxyphenyl)cyclohexanol and trans-(1S,2R)-2-(2'-benzyloxyphenyl)cyclohexanol to obtain trans-(1R,2S)-2-(2'-hydroxyphenyl)cyclohexanol and trans-(1S,2R)-2-(2'-hydroxyphenyl)cyclohexanol;

(e) independently chiral ring closing the trans-(1R,2S)-2-(2'-hydroxyphenyl)cyclohexanol and trans-(1S,2R)-2-(2'-hydroxyphenyl)cyclohexanol with p-toluenesulfonyl halide/pyridine or p-toluenesulfonic acid or ester to obtain. [5a(S),9a(S)-(5a,6,7,8,9,9a-hexahydro)]dibenzofuran and [5a(R)-,9a(R)-(5a,6,7,8,9,9a-hexahydro)]dibenzofuran

* * * * *